United States Patent [19]

Luther et al.

[11] 4,377,165
[45] Mar. 22, 1983

[54] CANNULA NEEDLE FOR CATHETER

[75] Inventors: Ronald B. Luther, Newport Beach, Calif.; Peter F. Frey, Buergenstock, Switzerland; Marshall F. Sparks, Santa Ana, Calif.

[73] Assignees: Luther Medical Products, Inc., Costa Mesa, Calif.; Cobra, Inc., Ennetbuergen, Switzerland

[21] Appl. No.: 271,663

[22] Filed: Jun. 8, 1981

[51] Int. Cl.³ ............................................. A61M 5/00
[52] U.S. Cl. .................................. 128/214.4; 128/221
[58] Field of Search ............ 128/214 R, 214.4, 350 R, 128/221, 345; 29/413, 417, DIG. 32, DIG. 33, DIG. 40, DIG. 49, 509

[56]  References Cited

U.S. PATENT DOCUMENTS

| | | | |
|---|---|---|---|
| 3,124,872 | 3/1964 | Knodel, Jr. | 29/413 |
| 3,330,278 | 7/1967 | Santomieri | 128/214.4 |
| 3,359,978 | 12/1967 | Smith | 128/214.4 |
| 3,592,193 | 7/1971 | Higgins | 128/221 |
| 3,596,658 | 8/1971 | Lange | 128/221 |
| 3,651,807 | 3/1972 | Huggins | 128/221 |
| 3,766,915 | 10/1973 | Rychlik | 128/221 |
| 4,243,495 | 1/1981 | Trott | 29/413 X |

FOREIGN PATENT DOCUMENTS 2715198  11/1977  Fed. Rep. of Germany ... 128/214.4

*Primary Examiner*—Richard J. Apley
*Assistant Examiner*—Michelle N. Lester
*Attorney, Agent, or Firm*—Willie Krawitz

[57]   ABSTRACT

A cannula needle for a catheter is provided from flat metal sheet blank stock. A groove of controlled depth is formed on the metal sheet which is then rolled to produce a hollow barrel having a slit parallel to the longitudinal axis; the barrel is then cut into individual needles. Gripping wings are then welded to each needle on either side of the slit in a separate operation.

In use, when the wings are flexed, the needle will easily split in half along the groove. This enables the cannula to be separated from the catheter.

12 Claims, 8 Drawing Figures

CANNULA NEEDLE FOR CATHETER

BACKGROUND OF THE INVENTION

This invention relates to a continuous process for the manufacture of a new and improved cannula needle. The needle is adapted for use with a catheter which is passed therethrough for insertion into a patient. The needle is then withdrawn from the patient and separated from about the catheter that remains in place.

A very large number of patients are treated in this fashion throughout the world. It would be highly desirable to manufacture a reliable and inexpensive cannula needle at high production rates to accommodate typical catheters used in these treatments. Preferably, there is desired a one-piece cannula needle that can be readily manipulated for insertion into a patient and then be easily broken apart and separated from about the catheter.

One type of guide needle for a catheter is disclosed in U.S. Pat. No. 3,359,978 to Raymond M. Smith. That needle is manufactured from steel flat stock that has been stamped in a one-shot operation to form a needle pattern, reinforcing roof and handles or wings. A groove or trough is formed in the flat stock during the stamping operation, and the flat stock is then rolled to a circular needle configuration. In use, the handles are flexed to open the needle, and the open needle is then separated from the catheter. Alternatively, flat sheet stock is formed into a tube, and two grooves are milled on the tube exterior. In use, the handles are flexed to split open the needle along the upper groove, while the lower groove functions as a hinge; the needle is then separated from about the catheter.

While the Smith needle is simple and inexpensive, it has not been commercialized. The problem arises because it is extremely difficult to manufacture a single groove of uniform depth using a stamping operation. This type of groove impairs a uniform and controlled opening of the needle. Alternatively, if two grooves are machined on a tube, the upper groove must be sufficiently deep to split open easily, and the lower groove must be deep enough to permit hinge flexing, but not too deep to avoid premature splitting.

Consequently, in both cases when the needle is flexed open, there is an excessive variation in the opening or flex properties between needle batches and even between individual needles, and this variation is unacceptable to the user, generally a nurse.

There is desired a cannula needle for use with a catheter, the cannula being continuously grooved and formed from flat sheet metal stock, rolled, and then cut into a needle configuration. The groove should be sufficiently deep so that when flexed open, the needle will easily split away from the catheter in a uniform manner and usually in a single motion. Conventional means preferably should be used to form the groove continuously such as by cold rolling, cutting with a diamond, etc.

To facilitate working of the metal stock into a grooved, rolled and cut form, the flexing wings must be attached to the needle in a separate operation, and this may be done by laser or resistance welding, etc. A form of laser welding is described in U.S. Pat. No. 4,100,393 to Ronald B. Luther.

THE INVENTION

According to the invention, there is provided a process for producing a cannula needle and a new and improved cannula needle therefrom. The process comprises continuously forming a needle blank from flat sheet metal such as sections or from a roll. A groove of controlled depth is formed along the blank stock which is then rolled to a hollow configuration and then cut into individual needle barrels with a longitudinal slit along each needle barrel. The groove is oriented parallel to the slit and along the opposite side of the barrel. Finally, the wings are welded to the barrel on each side of the slit.

It is a major feature of this invention that only one groove is employed, and its depth is readily controlled when using a continuous process. The groove depth is sufficiently shallow to ensure adequate stiffness during use, and eliminates the need to produce a reinforcing roof. However, the groove is made deep enough so that the needle will split easily when the wings are flexed; the needle is then separated from the catheter.

A second major feature of this invention is that the process for manufacturing the needle is related to the functioning of the needle itself. Specifically, the process forms the needle from the flat sheet stock into a split circular shape, and the split portion becomes the longitudinal, non-welded slit. Consequently, when in use, the requirement of flex forces to break apart this open slit side of the needle is completely eliminated. This construction of course makes it much easier for the user.

Excellent stiffness, splitting and rolling properties are obtained with a sheet thickness of about 2–4 mils, a needle length of about ¾"–2", about a 12–20 gage barrel diameter, and a controlled groove depth about 50%±10% of the sheet thickness using a 304–316 stainless steel or equivalent.

The sheet stock may be in flat form such as in sections, say, ½–10 feet long, but is usually loaded on a roll. The open needle portion constitutes only about 7%–15% of the total barrel length, and this considerably improves the working strength of the needle. By comparison, the Smith needle has an open barrel portion about 30% of the total barrel length. Thus, the needle of this invention can employ a relatively deeper groove without losing structural integrity during use.

DESCRIPTION OF THE PREFERRED EMBODIMENTS

Figure 1:
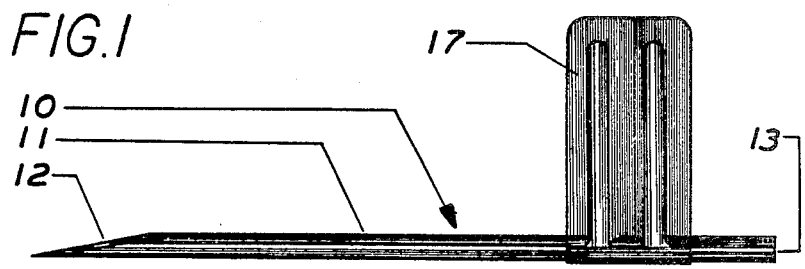
FIG. 1 is an external view in side elevation showing an assembled needle according to the invention, with attached flexing wings.
Figure 2:
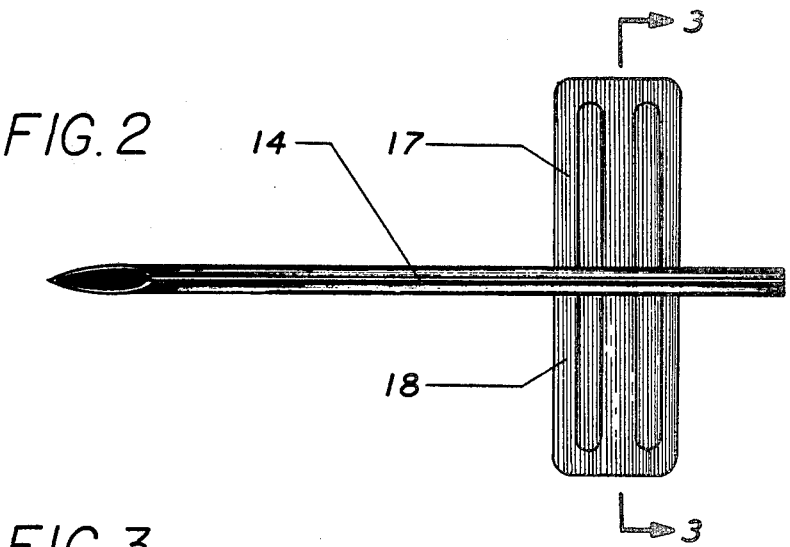
FIG. 2 is a plan view of the assembled needle showing the longitudinal slit between the edges of the blank after rolling into the needle configuration.
Figure 3:
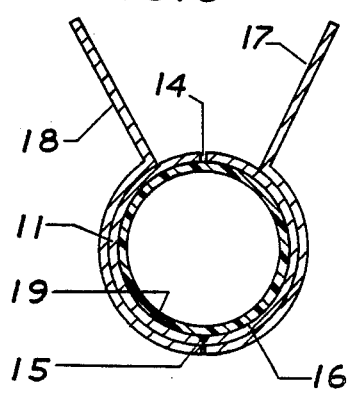
FIG. 3 is an enlarged cross section view of the needle taken along the lines 3—3 of FIG. 2.

The cannula needle 10 of this invention is shown in FIGS. 1, 2 and 3 after it has been worked from a flat metal strip and attachment of wings. The flat strip working involves grooving, cold rolling into a hollow shape and then cutting to produce individual needle barrels, and is illustrated in FIGS. 5-8.

The barrel 11 defines a needle end 12, an end portion 13, and a longitudinal slit 14, extending along the barrel. The slit 14 is formed when the blank is rolled to produce the barrel, and a typical slit varies from about 0-1 mil wide. As shown in FIG. 3, the groove 15 is formed on the inside wall 16 of the needle and extends longitudinally of the needle from end to end; the groove 15 is located about 180° radially from the slit 14 and is parallel thereto. Flexing wings 17, 18 are mounted rearwardly of the barrel and are attached using laser or resistance welding, etc.; this is a separate step from the flat strip working.

Figure 4:
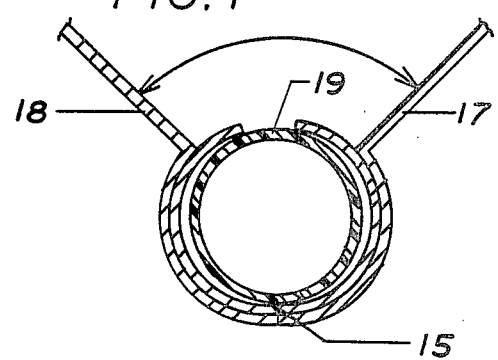
FIG. 4 is a cross section view of the needle showing the effects of flexing the wings to split the needle and thereby separate the needle from the catheter.

As shown in FIG. 4, when the wings are flexed in the direction shown by the arrows, the needle will open up along the longitudinal slit 14, and split or crack along the groove 15, usually with one or two motions of the wings. The needle halves are then separated from the catheter 19.

Figure 5:
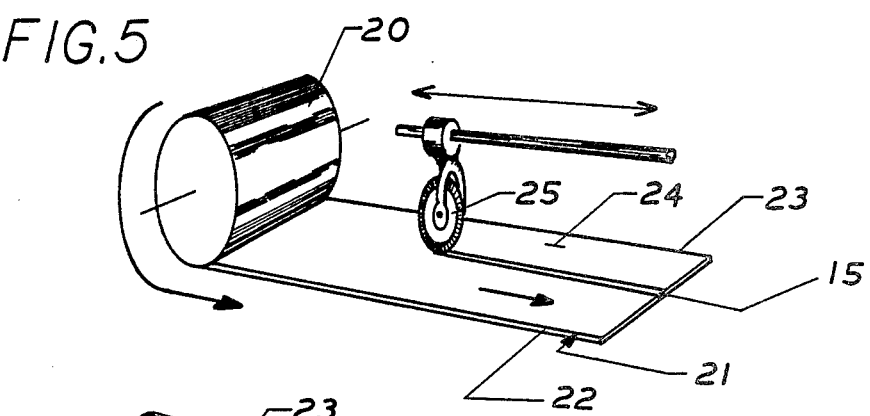
FIG. 5 is a schematic view showing one embodiment of the groove forming operation on the sheet flat stock.
Figure 6:
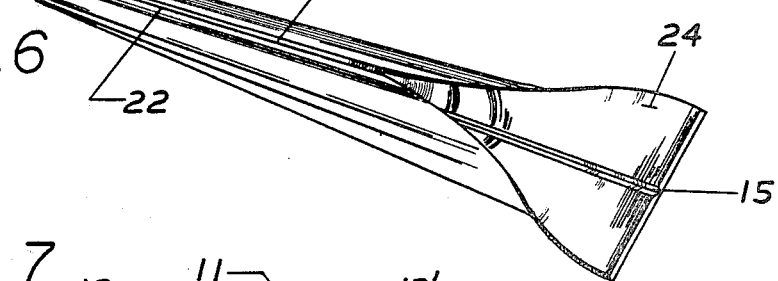
FIG. 6 is a perspective view illustrating a partially rolled needle barrel according to the invention.

Manufacture of the cannula 10 of this invention is illustrated in FIGS. 5-8. In FIG. 5, a roll 20 of flat sheet metal stock 21 having edges 22, 23 is shown being unwound in the direction of the arrow. The groove 15 is indented onto the upper face 24 by movement of a metal pressure roller 25, and the groove depth may be controlled using an apparatus similar to that shown in FIG. 8. In FIG. 6, when the grooved sheet 21 is rolled into a barrel configuration, the upper face 24 becomes the inside wall 16 of the barrel 11 illustrated in FIG. 3, and the edges 22, 23 are rolled adjacent to each other and form the slit 14. The groove 15 and slit 14 are parallel to each other about 180° radially apart, and are formed longitudinally along the barrel.

Figure 7:
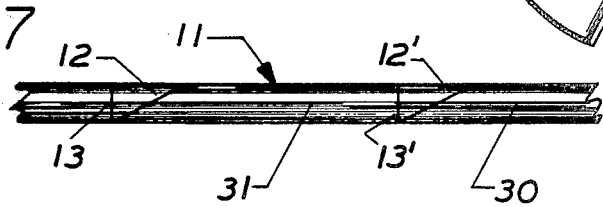
FIG. 7 is an external side elevation view showing the needle cut lines on the grooved and rolled barrel; and, FIG. 8 is a schematic view illustrating a pressure sensor and actuator for controlling the groove depth during manufacture.

In FIG. 7, the barrel 11 is shown after it has been completely rolled. Individual needles 30, 31 are cut to form the needle ends 12, 12', and end portions 13, 13'; the wings are then welded to the individual needle barrels.

Figure 8:
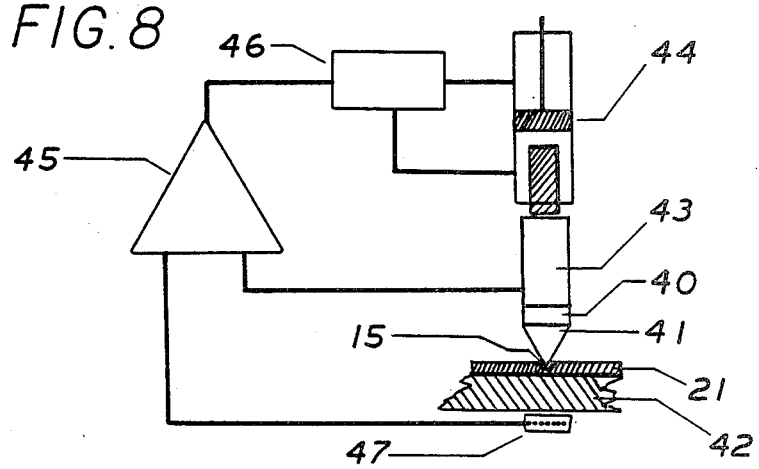

FIG. 8 illustrates another type of apparatus used to control groove depth. This comprises a stylus 40 and diamond scribe 41 at the stylus end to cut (rather than indent) the groove 15 on the flat stock 21 shown on a support 42. A pressure sensor 43 is provided upwardly of the stylus, and a pneumatic/hydraulic pressure applicator 44 is mounted upwardly of the sensor. A comparator 45 is pre-set to determine variations in desired versus actual pressure as determined by the sensor which feeds back an appropriate signal to a driver/controller 46. The controller will cause the applied force of the pressure applicator 44 to vary and thereby produce a groove of uniform depth. If say, a Hall effect sensing is desired, a sensor 47 is used to produce a signal that is fed to the comparator 45.

It will be appreciated that various equivalent embodiments of this invention are possible without departing from the spirit thereof. For example, if sheet metal of a type other than the 304-316 stainless steel is employed, a different thickness and groove depth may be required. Also, it might be useful to roll the flat stock so that the groove is oriented on the outside rather than on the inside of the barrel wall. Furthermore, other barrel configurations may be utilized rather than simply a round shape. Finally, various barrel diameters, barrel lengths and barrel thicknesses may require different groove depths and different lengths of open needle portions relative to the overall length of the barrel to achieve the desired results, but these parameters can be readily determined.

We claim:

1. A breakaway cannula needle for insertion of a catheter therethrough, comprising:
   (a.) a barrel portion defining inner and outer walls, and a central longitudinal axis, the barrel being formed by cold rolling from a flat blank of stainless steel sheet metal stock having outer parallel edges;
   (b.) a longitudinal slit about 0-1 mil wide defined along the barrel portion parallel to the longitudinal axis, and formed between the edges of the rolled blank, the slit defining opposed edges in parallel registry;
   (c.) a continuous groove formed on the inside wall of the barrel about 180° radially of the slit and parallel thereto, at a controlled and uniform depth of about 50% ± 10% of the flatstock thickness by rolling means;
   (d.) a needle portion provided at one end of the barrel, and defining a forward and rearward end, the slit extending along the barrel to one needle end, and the groove extending along the barrel to the other needle end; and,
   (e.) flexing wings attached to the cannula on each side of the slit;
   the flat sheet metal stock being initially grooved in a continuous manner followed by the sequential steps of:
      i. cold rolling the barrel; ii. segmenting to form the needle portion; and, iii. attaching the wings;
   whereby, the cold rolling work hardens the barrel and embrittles the groove, thereby enabling splitting of the needle along the groove in a uniform manner, and with needle-to-needle uniformity, when the wings are flexed, to enable separation of the needle from the cannula.

2. The cannula of claim 1, in which the sheet metal is 304-316 stainless steel having a thickness of about 2-4 mils, the needle is about ¾"-2" long, and a diameter of about 12-20 gage.

3. The cannula needle of claim 2, in which the open needle portion constitutes up to about 15% of the total barrel length.

4. The cannula of claim 1, defining an open needle portion of about 7%-15% of the barrel along its length.

5. The cannula of claim 1, in which a needle portion is provided at one end of the barrel, the needle portion defining a forward and a rearward end, the slit extending along the barrel to the rearward end of the needle, and the groove extending along the barrel to the forward end of the needle.

6. The cannula of claim 1, in which the sheet metal is 304-316 stainless steel, having a thickness of about 2-4 mils, and a barrel diameter up to about 12 gage.

7. The cannula of claim 1, in which the sheet metal is 304-316 stainless steel and the barrel diameter is up to about 12 gage.

8. The cannula needle of claim 1, in which the groove is formed by a pressure roller.

9. The cannula needle of claim 1, in which the flexing wings are welded to the cannula.

10. The cannula needle of claim 9, in which the flexing wings are laser welded to the cannula.

11. The cannula needle of claim 1, in which the flexing wings are resistance welded to the cannula.

12. The cannula needle of claim 1, in which the sheet metal is 304 stainless steel.

* * * * *